(12) United States Patent
Nogami et al.

(10) Patent No.: US 9,128,070 B2
(45) Date of Patent: Sep. 8, 2015

(54) ANALYSIS DEVICE

(75) Inventors: Makoto Nogami, Tsuchiura (JP);
Katsuhiro Kanda, Hitachinaka (JP);
Shinya Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/580,249

(22) PCT Filed: Jan. 14, 2011

(86) PCT No.: PCT/JP2011/000160
§ 371 (c)(1),
(2), (4) Date: Aug. 21, 2012

(87) PCT Pub. No.: WO2011/108177
PCT Pub. Date: Sep. 9, 2011

(65) Prior Publication Data
US 2012/0322139 A1    Dec. 20, 2012

(30) Foreign Application Priority Data

Mar. 3, 2010    (JP) .................................. 2010-046066

(51) Int. Cl.
*G01N 27/62* (2006.01)
*C12M 1/42* (2006.01)
*G01N 35/00* (2006.01)
(Continued)

(52) U.S. Cl.
CPC .......... *G01N 35/0098* (2013.01); *G01N 35/025* (2013.01); *G01N 2035/1053* (2013.01)

(58) Field of Classification Search
CPC ................... G01N 35/0098; G01N 2035/1053
USPC .......................................................... 422/64
See application file for complete search history.

(56) References Cited

U.S. PATENT DOCUMENTS 5,585,068 A * 12/1996 Panetz et al. .................... 422/64
2002/0009394 A1   1/2002 Koster et al.
(Continued)

FOREIGN PATENT DOCUMENTS

CN    201072391 Y    6/2008
JP    05-080059    *    3/1993
(Continued)

OTHER PUBLICATIONS

Lopez et al.; "Selected Reaction Monitoring-Mass Spectrometric Immunoassay Responsive to Parathyroid Hormone and Related Variants"; Clinical Chemistry; 2010; pp. 281-290; vol. 56; No. 2.
(Continued)

*Primary Examiner* — P. Kathryn Wright
*Assistant Examiner* — Julie Tavares
(74) *Attorney, Agent, or Firm* — Mattingly & Malur, PC

(57) ABSTRACT

Disclosed is an analysis device which can analyze substances with low blood concentration with high precision without having to make the device larger. The analysis device is composed of: a specimen disk equipped with specimen containers; a reagent disk equipped with reagent containers; a first disk equipped with first containers where purification of the subject component to be measured in the specimen is carried out; a second disk equipped with second containers where purification of the sample purified in the first container is carried out; and a mass spectrometry unit which measures the specimen purified in the second container.

7 Claims, 5 Drawing Sheets

(51) Int. Cl.
*G01N 35/02* (2006.01)
*G01N 35/10* (2006.01)

(56) References Cited

U.S. PATENT DOCUMENTS

| 2008/0217254 | A1 | 9/2008 | Anderson |
| 2009/0081794 | A1* | 3/2009 | Wakamiya et al. ............. 436/43 |
| 2011/0111443 | A1 | 5/2011 | Nishimura et al. |

FOREIGN PATENT DOCUMENTS

| JP | 05-080059 | A | 3/1993 |
| JP | 11-201953 | A | 7/1999 |
| JP | 2002-541459 | A | 12/2002 |
| JP | 2004-093194 | A | 3/2004 |
| JP | 2005-524394 | A | 8/2005 |
| JP | 2006007081 | A * | 1/2006 |
| JP | 2007-232501 | A | 9/2007 |
| JP | 2009-294118 | A | 12/2009 |
| WO | 03/087772 | A2 | 10/2003 |
| WO | 2009/044900 | A1 | 4/2009 |

OTHER PUBLICATIONS

Kumar et al.; "Quantification of Serum 1-84 Parathyroid Hormone in Patients with Hyperparathyroidism by Immuocapture in Situ Digestion Liquid Chromatography-Tandem Mass Spectrometry"; Clinical Chemistry; 2010; pp. 306-313; vol. 56; No. 2.

Hendriks et al.; "Standardized Comparison of Processing Capacity and Efficiency of Five New-Generation Immunoassay Analyzers"; Clinical Chemistry; 2000; pp. 105-111; vol. 46; No. 1.

Chinese Office Action received in corresponding Chinese Application No. 201180010363 dated Sep. 4, 2014.

* cited by examiner

POSITION A
POSITION B
POSITION C
POSITION D
101
102

102
101
902
901

ANALYSIS DEVICE

TECHNICAL FIELD

The present invention relates to an analysis device, particularly, relates to an analysis device combining purification by an antigen-antibody reaction, and detection by mass spectrometry.

BACKGROUND ART

A physiologically active substance such as protein, peptide, hormone and a metabolite thereof is a substance carrying information transmission to adjust action of a specific organ in vivo, and thus fulfilling an important role in life activity. Therefore, it is important to inspect concentration of the physiologically active substance in a specific disease. For example, there has been reported that there is relation between increase and decrease in estrogen, which is a female hormone, and risk of breast cancer. The physiologically active substance exerts action thereof in quite a small amount, and concentration in a body is very low level of pg/mL to ng/mL. Accordingly, there has been required a method for quantifying the physiologically active substance in an organism sample, simply and accurately.

As one of the methods for quantifying the physiologically active substance, there is immunoassay. An automatic analysis device using the immunoassay enables to provide random access, and high throughput, therefore it has been used widely as a clinical laboratory test device (PATENT LITERATURE 2). For example, in the immunoassay, detection is performed by utilization of an antibody which specifically recognizes a subject component to be measured, for example, by capturing the subject component to be measured in a specimen using the antibody (a primary antibody), and then by utilizing a secondary antibody which further selectively captures the above primary antibody. On the other hand, it has been known generally that cross-reactivity is generated in the immunoassay. The cross-reactivity is a phenomenon where the primary antibody captures not only the subject component to be measured which the primary antibody should originally captures but also molecules having a similar structure, for example, a metabolite of the subject component to be measured or the like. In particular, the physiologically active substance is a low molecular weight substance, and has low specificity of antibody recognition, therefore the cross reaction appears.

In addition, application of mass spectrometry to clinical laboratory tests has also been prevailed, and it has been used as a method for quantifying the physiologically active substance. Because the mass spectrometry is measured based on the mass of a subject component, it is a measurement technology that identification is possible from, for example, a molecule having a similar structure of a metabolite or the like. An MRM (Multiple Reaction Monitoring) mode of a triple quadrupole mass spectrometer, having particularly high selectivity, is a method for passing through only a precursor ion at a quadrupole of the first stage, cleaving this ion at the next collision cell, and monitoring only a product ion specific to the compound at a quadrupole of the second stage. This method provides mass to charge information specific to a compound, and enables the relative quantification of the subject component to be measured, by correction with an internal standard substance which had been added in advance and has known concentration.

There has been disclosed PATENT LITERATURE 1 in which the antigen-antibody reaction and the mass spectrometry are applied, aiming at quantification of protein. In this method, firstly, by adding an enzyme to a specimen of serum or the like, protein is digested to peptide. Next, by adding and reacting antibody magnetic beads immobilized with an anti-peptide antibody and an internal standard substance labeled with a stable isotope to peptide which is a subject component to be measured, the peptide which is the subject component to be measured and the internal standard substance are bound to the antibody magnetic beads. After that, a treated specimen is introduced to a device which can concentrate the subject component to be measured and detect by mass spectrometry, and thus the quantification of peptide is performed. As for the composition of this device, tubing is connected via a plurality of valves at the former stage, and a magnet is arranged at the exterior side of a part of tubing. The concentrated peptide is ionized using an electrospray ionization method (ESI), to perform analysis using liquid chromatography/mass spectrometry (LC-ESI-MS). This device enables the concentration of the subject substance to be measured bound with the antibody magnetic beads, desorption from the antibody magnetic beads, and online detection using the mass spectrometer. In NON PATENT LITERATURE 1, analysis of peptide having physiologically active action is performed by applying the antigen-antibody reaction and the mass spectrometry. Protein, which is the subject substance to be measured, is made bound and concentrated by using polystyrene beads immobilized with the antibody. The analysis is performed using mass spectrometry (MS), by enzymatic digestion of the concentrated protein, cleaving it to peptide which is the subject substance to be measured, and ionizing using matrix-assisted laser desorption ionization (MALDI). In NON PATENT LITERATURE 2, although the steps of the antigen-antibody reaction and the enzymatic digestion are similar, analysis is performed by liquid chromatography/mass spectrometry (LC-ESI-MS) by ionization using the electro-spray ionization method (ESI). The steps up to the enzymatic digestion are processed, for example, in a 96-well plate, using an automatic pipette tool to enhance throughput.

CITATION LIST

Patent Literature

PATENT LITERATURE 1: US 2008/0217254 A1
PATENT LITERATURE 2: JP-A-5-80059

Non Patent Literature

NON PATENT LITERATURE 1: M. F. Lopez, et. al., Selected Reaction Monitoring-Mass Spectrometric Immunoassay Responsive to Parathyroid Hormone and Related Variants, Clin. Chem., 56, 2, 281-290, 2010
NON PATENT LITERATURE 2: V. Kumar, et. al., Quantification of Serum 1-84 Parathyroid Hormone in Patients with Hyperparathyroidism by Immunocapture In Situ Digestion Liquid Chromatography-Tandem Mass Spectrometry, Clin. Chem., 56, 2, 306-313, 2010
NON PATENT LITERATURE 3: H. A. Hendriks, et. al., Standardized Comparison of Processing Capacity and Efficiency of Five New-Generation Immunoassay Analyzers, Clin. Chem., 46, 1, 105-111, 2000

SUMMARY OF INVENTION

Technical Problem

However, the conventional methods such as those disclosed in the PATENT LITERATURE 1, the NON PATENT LITERATURE 1 and the NON PATENT LITERATURE 2 had problems in "measurement precision", "throughput" and "installation area of the device".

Explanation will be given on the problem of "measurement precision". In the case of quantification of the physiologically active substance by the method of the PATENT LITERATURE 1, the enzymatic digestion and steps for binding the antibody magnetic beads and the physiologically active substance (peptide in the PATENT LITERATURE 1) are manual methods. Therefore, depending on the difference of the maneuver of measurers caused by suction/discharge of a specimen, reaction time with the antibody magnetic beads, stirring speed or the like, it becomes a factor of varying data, which makes it difficult to obtain accurate quantitative values. Similarly, in the NON PATENT LITERATURE 1 and the NON PATENT LITERATURE 2, the step for adding a sample to a plate, and the step for transporting a treating solution to introduce the sample after the enzymatic digestion processing to the mass spectrometer are manual methods, which therefore becomes a factor of varying data is depending on the difference of the maneuver of measurers.

In addition, in the PATENT LITERATURE 1, the steps up to the concentration, desorption and mass spectrometry of the physiologically active substance bound to the antibody magnetic beads are performed on line. Therefore, an extremely trace amount of the physiologically active substance is transferred to inside of the tubing, which causes a loss by adsorption to the inside of the tubing, as well as carry over and contamination in introducing a different specimen, which make it difficult to obtain accurate quantitative value. In addition, in application to a clinical laboratory test, a specimen is forced to be introduced continuously. That is, the tubing could be clogged by, for example, protein, lipid or the like contained in serum which are contained in the specimen, and in that case, maintenance work is generated, which requires a large amount of labor and time.

Explanation will be given below on the problem of "throughput". In the PATENT LITERATURE 1, in a device which is capable of concentrating the subject component to be measured and also detecting it by mass spectrometry, a tubing having an inner diameter of 50 to 300 μm is connected on line via a plurality of valves. In measurement by the methods of PATENT LITERATURE 1 and NON PATENT LITERATURE 2, analysis is performed using liquid chromatography/mass spectrometry (LC-ESI-MS), therefore measurement time is long and thus 200 tests/hour (the NON PATENT LITERATURE 3), which is necessary throughput as a general clinical laboratory test device, cannot be attained. In NON PATENT LITERATURE 1, analysis is performed using mass spectrometer (MS) after ionization by matrix-assisted laser deionization method (MALDI), therefore the measurement time is short and the throughput relating to the measurement is high, however, because a time for pretreatment is required, such as drying of liquid dropped on an MALDI plate, so that total run time cannot be shortened. Therefore, it takes a long measuring time and is not suitable for clinical laboratory test application which requires, for example, 200 tests/hour.

Explanation will be given on the problem of "installation area of the device". To enhance the throughput, the present devices should be aligned in parallel. In that case, it is obvious that the installation area of the devices and cost increase.

By making it possible to provide a device and a method enabling simple and accurate quantification in detection of a physiologically active substance, they can be applied to a clinical field, thus realizing new approaches to various diseases caused by increase and decrease in the hormone in vivo.

It is an object of the present invention to provide the analysis device and the analysis method enabling simple quantification, even for the subject component to be measured with a low concentration of about pg/mL to ng/m level in blood.

Solution to Problem

Explanation will be given simply, as follows, on the outline of a typical one among inventions disclosed in the present application.

That is, the analysis device of the present invention is the analysis device, characterized by containing: a specimen disk equipped with specimen containers; a reagent disk equipped with reagent containers; a first disk equipped with first containers for performing purification of a subject component to be measured of the specimen; a second disk equipped with second containers for performing purification of the purified specimen in the first container; and a mass spectrometry unit for measuring the specimen purified in the second container. For example, in the first disk, a step for binding the antibody magnetic beads and the physiologically active substance is performed, and in the second disk, a step for binding of the physiologically active substance is performed using a solid phase extraction cartridge. The specimen concentrated by the antibody magnetic beads in the first disk cannot be introduced directly to the mass spectrometry unit, as it is, because contamination of impurities such as a salt, or ionization condition such as pH are not suitable for ionization. Therefore, in the second disk, the purification of the physiologically active substance should be carried out by the solid-phase extraction cartridge.

Advantageous Effects of Invention

Explanation will be given briefly, as follows, on effects obtained by a typical one among inventions disclosed in the present application.

That is, in the first disk, the first purification is performed, and in the second disk, purification is performed again for the specimen purified in the first disk. The first disk and the second disk are connected off line, a sample after the completion of purification in the second disk also can be introduced off line to a device such as, for example, a mass spectrometer. That is, random access becomes possible, and it is suitable for the clinical laboratory test applications.

In this way, analysis of an item of a low blood concentration, whose detection was difficult in a mass spectrometry unit, due to insufficient purification, is possible without making the device larger by performing the purification two times.

DESCRIPTION OF EMBODIMENTS

Explanation will be given below in detail on embodiments of the present invention with reference to drawings. It should be noted that, in all of the drawings for illustrating the present embodiment, ones having the same function is furnished with the same reference codes in principle so as to omit repeated explanation thereof as possible.

It should be noted that explanation will be given on a disk system, as an example, as a carrying mechanism for specimens or a reagents, however, it should not be limited thereto, and it may also be a carrying mechanism such as a belt conveyor. The present invention is mainly characterized by being provided with a mechanism for carrying out purification in two stages, when specimen concentration is low.

Example 1

Figure 1:
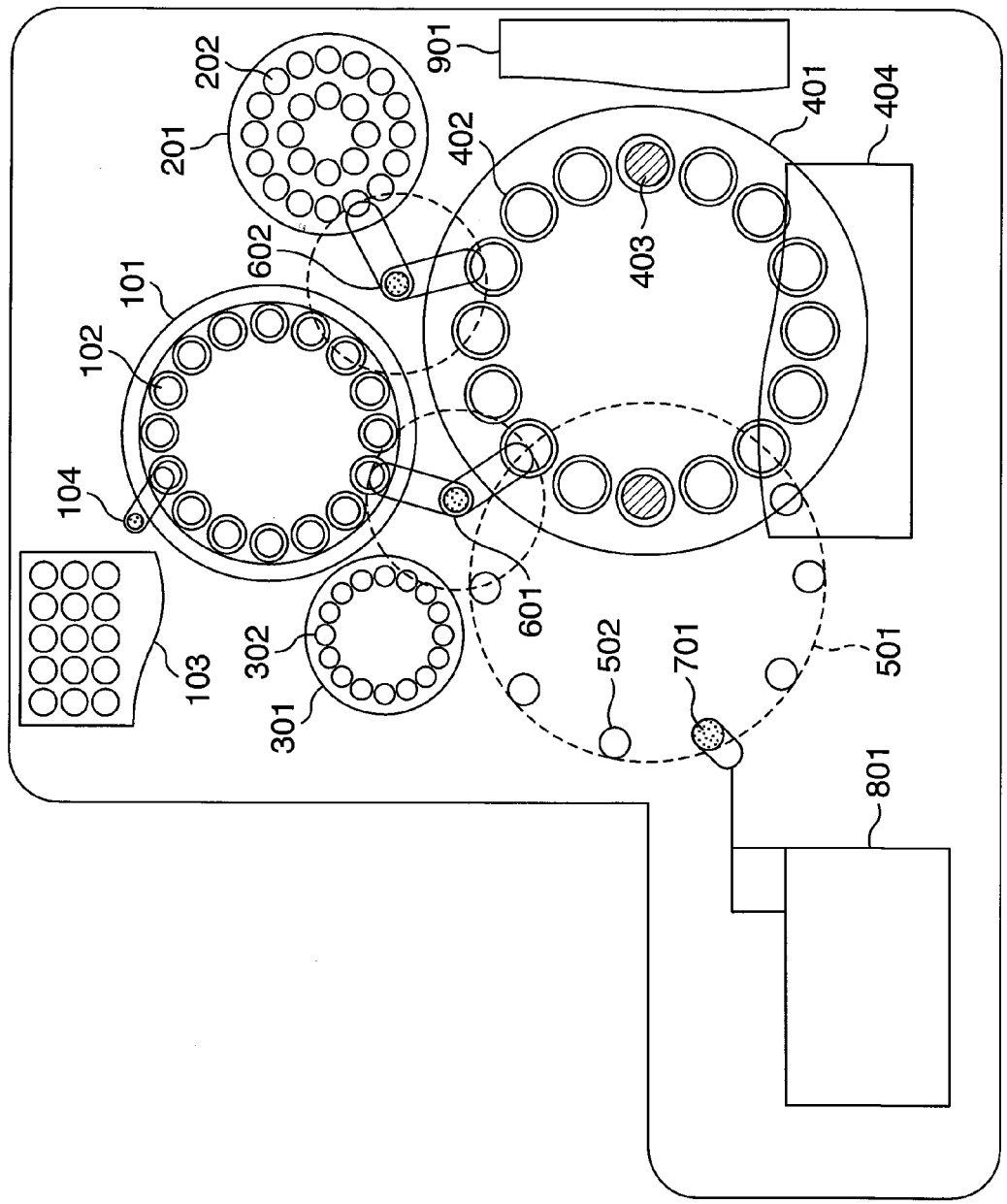
FIG. 1 is a schematic plan view showing an outline of one embodiment of the analysis device of the present invention combining purification by antigen-antibody reaction and detection by mass spectrometry.
Figure 2:
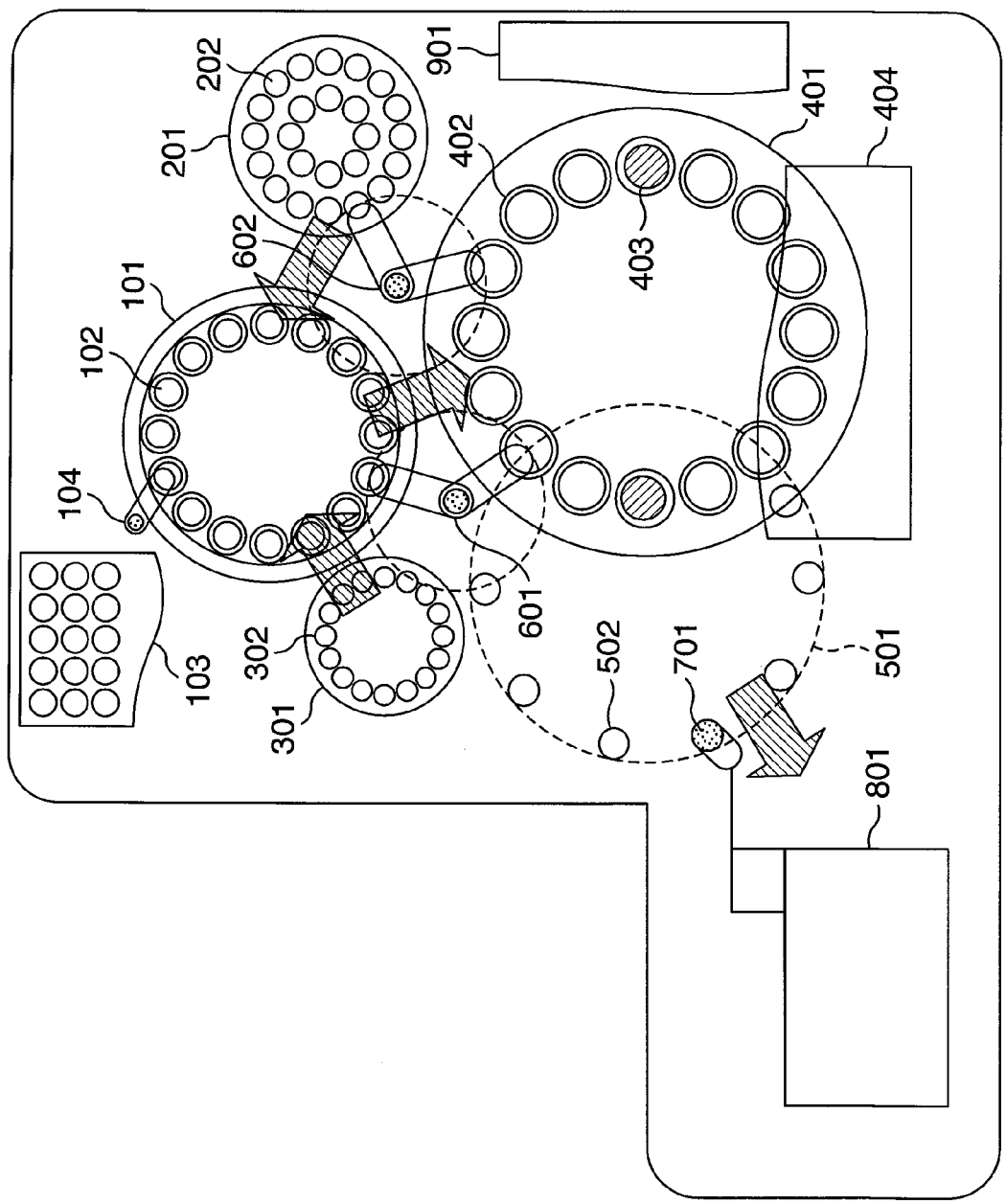
FIG. 2 is a drawing illustrating an action flow in the analysis device of FIG. 1.
Figure 3:
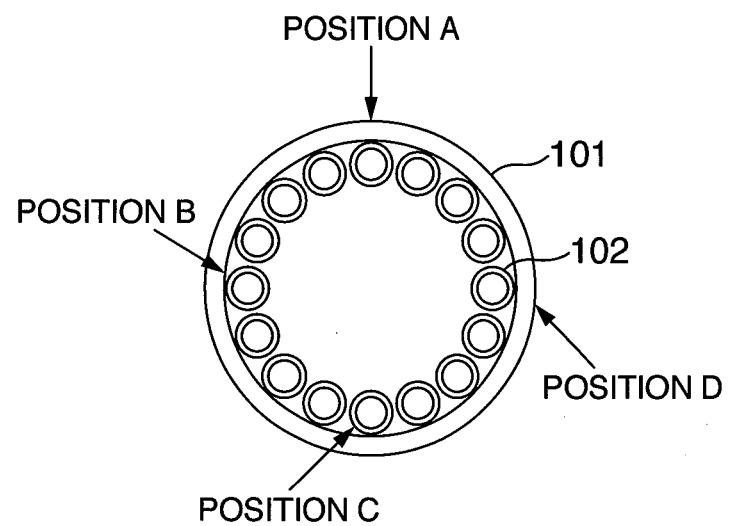
FIG. 3 is a drawing illustrating a relation between the position and the action of a disposable container of a specimen concentration disk.
Figure 4:
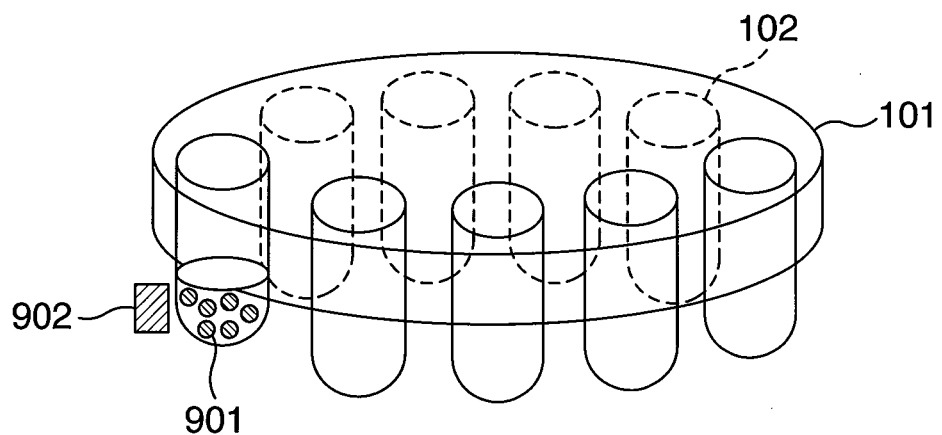
FIG. 4 is a side view showing an outline of a form of a specimen concentration disk.

FIG. 1 is a schematic plan view showing outline of one embodiment of the analysis device of the present invention combining purification by an antigen-antibody reaction, and detection by mass spectrometry, and FIG. 2 is a drawing illustrating a work flow in the analysis device of FIG. 1. FIG. 3 is a drawing illustrating a relation between the position and the action of a disposable container of a specimen concentration disk. FIG. 4 is a side view showing an outline of the form of the specimen concentration disk. In addition, depicting of a control unit, a display unit, an input unit and a memory unit is dared to be omitted in any of the drawings.

Explanation will be given on device composition of the present invention with reference to FIG. 1. The analysis device shown in FIG. 1 is provided with a specimen concentration disk 101, a reagent disk 201, a specimen disk 301, a solid-phase extraction cartridge disk 401, a saucer disk 501, a disposable container housing unit 103, a consumable housing unit 404, a mass spectrometry unit 801, a specimen probe 601 and a reagent probe 602.

In the specimen concentration disk 101, disposable containers 102 are arranged on a concentric circle at predetermined intervals. In the disposable container 102, by using magnetic beads bound with an antibody which specifically recognizes a subject component to be measured, in advance, by avidin-biotin binding, concentration of the subject component to be measured is performed. It should be noted that the specimen concentration disk 101 is maintained at the optimal temperature of the antigen-antibody reaction, and in the present Example, it is set at 37° C.

The reagent disk 201 is installed at the side of the specimen concentration disk 101 and the solid phase extraction cartridge disk 401, wherein reagent containers 202 for storing reagents are arranged on a concentric circle at predetermined intervals. As the reagent, an internal standard substance for the subject component to be measured, a suspension solution of the magnetic beads, a washing solution for washing impurities other than the subject component to be measured held in the magnetic beads, and an eluate for making the subject component to be measured elute from the magnetic beads are stored in the reagent containers 202, in a cooled state at about 10° C.

The specimen disk 301 is installed at the side of the specimen concentration disk 101 and the solid-phase extraction cartridge disk 401, wherein specimen containers 302 for storing specimens are arranged on a concentric circle at predetermined intervals.

The solid phase extraction cartridge disk 401 is installed at the side of the specimen concentration disk 101, the reagent disk 201 and the specimen disk 301, wherein solid-phase extraction cartridges 402 are arranged on a concentric circle at predetermined intervals. In the solid phase extraction cartridge 402, a specimen purified at the specimen concentration disk 101 is purified again. It should be noted that the solid-phase extraction cartridge disk 401, although depiction is omitted, is provided with a stirring mechanism for stirring the specimen or the specimen concentrated at the specimen concentration disk 101 with an internal standard substance or the reagent, and a liquid level detection mechanism for detecting a liquid level in the extraction of a solid-phase extraction cartridge, that is, a progress status of the solid extraction, for example, by using a CCD camera or the like. In addition, the purification operation at the solid-phase extraction cartridge 402 is composed of 5 steps: a step for conditioning a solid phase of the solid-phase extraction cartridge 402, a step for equilibrating the solid phase, a step for making the specimen adsorb to the solid phase, a step for washing the solid phase and a step for making the purified specimen elute from the solid phase. To pass through a solution from upward to downward of the solid phase in each step, a pressure loading unit 403 is provided at upward of the solid phase extraction cartridge 402.

Figure 6:
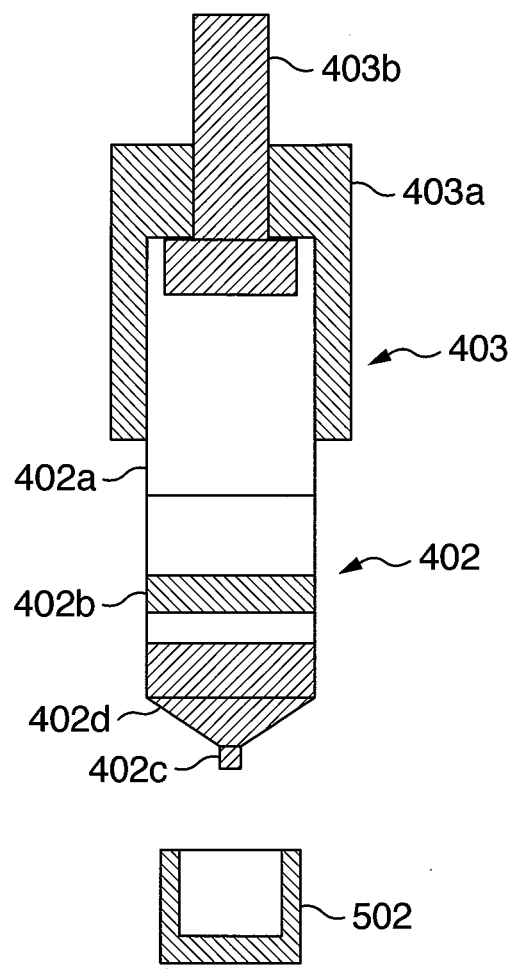
FIG. 6 is a block diagram showing a composition of a pressure loading unit to be used in an inspection device.

The solid-phase extraction cartridge 402 is composed of a cartridge main body 402a, an upper-stage filter 402b, a lower-stage filter 402c and a solid-phase extraction agent 402d, as depicted in FIG. 6. The solid-phase extraction agent 402d is sandwiched between the upper-stage filter 402b and the lower-stage filter 402c, and is held inside of the cartridge main body 402a. The solid-phase extraction agent 402d may use a filler generally called as a reversed phase system, having an action of adsorbing an immunosuppressive agent in a blood sample solution by hydrophobic interaction. For example, fine particles added with an octadecyl group at the surface of an organic polymer may be used. As the upper-stage filter 402b and the lower-stage filter 402c, for example, one having a pore diameter of about 1.0 μm is used.

The pressure loading unit 403 is provided with a pressure loading unit holder 403a and a syringe for pressurization 403b. The pressure loading unit holder 403a is mounted at the upper part of the solid-phase extraction cartridge 402 without a gap.

By transferring the syringe for pressurization 403b to the side of the solid-phase extraction cartridge 402 (in a downward direction of FIG. 6), a gas in the cartridge is compressed to increase the pressure in the cartridge. By the pressurization, a solution is discharged to outside through the lower-stage filter 402c.

The saucer disk 501 is arranged downward the solid-phase extraction cartridge disk 401, wherein saucer containers 502, capable of capturing an eluate eluted from the downward of the solid-phase extraction cartridge 402, are arranged on a concentric circle at predetermined intervals. When viewed from the upward, at least two positions of the solid-phase extraction cartridge 402 and the saucer container 502 are overlapped. In this way, because a space is generated at the upward of the saucer container, such a composition is attained where access to a specimen after purification is easy.

The disposable container housing unit 103 is installed at the side of the specimen concentration disk 101. The disposable container 102 is transported using a disposable container transport mechanism 104, and installed at the specimen concentration disk 101.

The consumable housing unit 404 is installed at the side of the solid-phase extraction cartridge disk 401. The solid-phase extraction cartridge 402 and the saucer containers 502, which are consumable, are installed from the consumable housing unit 404 to the solid-phase extraction cartridge disk 401 and the saucer disk 501, respectively.

The specimen probe 601 is provided with a specimen dispensing mechanism for performing the suction/discharge of liquid, and is installed at the side of the specimen concentration disk 101, the specimen disk 301 and the solid-phase extraction cartridge disk 401. The specimen probe 601 has a working range enabling the suction/discharge of a specimen from one of the disposable container 102 on the specimen concentration disk 101, one of the specimen container 302 on the specimen disk 301 and one of the solid-phase extraction cartridge 402 on the solid-phase extraction cartridge disk 401, while rotating. That is, the rotation orbit of the specimen probe 601 is to cross each of the rotation orbit of the specimen concentration disk 101, the rotation orbit of the specimen disk 301, and the rotation orbit of the solid phase extraction cartridge disk 401, at least at one point.

The reagent probe 602 is provided with a specimen dispensing mechanism for performing the suction/discharge of liquid, and is installed at the side of the reagent disk 201, the specimen concentration disk 101 and the solid-phase extraction cartridge disk 401. The reagent probe 602 has a working range enabling the suction/discharge of a specimen from one of the reagent container 202 on the reagent disk 201, one of the disposable container 102 on the specimen concentration disk 101, and one of the solid phase extraction cartridge 402 on the solid phase extraction cartridge disk 401, while rotating. That is, the rotation orbit of the specimen probe 601 is to cross each of the rotation orbit of the specimen concentration disk 101, the rotation orbit of the reagent disk 201, and the rotation orbit of the solid phase extraction cartridge disk 401, at least at one point.

A pretreated specimen introduction mechanism 701 is installed on the saucer disk 501 and is provided with a specimen dispensing mechanism for performing the suction/discharge of liquid. It can perform the suction of a specimen after completion of pretreatment from one saucer container 502 on the saucer disk 501, and the discharge to the mass spectrometry unit 801.

The mass spectrometry unit 801 is installed at the side of the saucer disk 501, and is provided with a pump for extruding a solution to introduce a sample to an ionization unit, the ionization unit for making the sample ionized by applying voltage, and a mass spectrometer for analyzing a subject substance to be measured.

Subsequently, explanation will be given on a work flow in the analysis device of FIG. 1. Explanation will be given, in the present Example, on analysis of 17β-estradiol, which is one kind of female hormone. The 17β-Estradiol is used also for prevention/treatment of osteoporosis. In addition, there is a report example describing that it is one of endocrine disrupters causing biological concentration to the water environment or fishes. In the present Example, a serum containing estradiol was used as a specimen. Analysis of whole blood, urine, saliva and a cell tissue other than serum are also possible as the specimen. It should be noted that the use of the present analysis device makes it possible to analyze hormones, anti-cancer agents, molecular target agents and metabolites thereof or the like, where the concentration of the subject component to be measured in the specimen is in a level of pg/mL or lower. In the case of analyzing these subject components to be measured, because purification operation only at the solid-phase extraction cartridge 402 leaves impurities and makes high precision analysis difficult due to insufficient sensitivity of the mass analysis device, precision can be increased by performing purification operation using the antibody magnetic beads 901 at the specimen concentration disk 101.

That is, in the case of analyzing the hormones, anti-cancer agents, molecular target agents and metabolites thereof or the like, where the concentration of the subject component to be measured in the specimen is in a level of pg/mL or lower, the specimen held in the specimen disk 301 should be added to the inside of the disposable container 102 installed at the specimen concentration disk 101. In addition, also as for the internal standard substance held in the reagent disk 201, it should be added to the inside of the disposable container 102 installed at the specimen concentration disk 101.

It should be noted that, on the other hand, as for antiepileptic drugs or antibacterial agents or the like, where the concentration of the subject component to be measured in the specimen is in a level of μg/mL or higher, purification using the antibody magnetic beads 901 at the specimen concentration disk 101 may not be performed. In that case, the specimen is transported not to the specimen concentration disk 101 but to the solid-phase extraction cartridge 402 installed at the solid-phase extraction cartridge disk 401. In addition, also as for the internal standard substance held in the reagent disk 201, it should be added to the inside of the solid-phase extraction cartridge 402 installed at the solid phase extraction cartridge disk 401.

Accordingly, the purification procedure may be changed in response to the specimen concentration. For example, it is also effective to control the analysis device as follows: by specifying the specimen concentration in advance, in the case where it is the predetermined concentration or higher, the specimen may be directly added to the inside of the solid phase extraction cartridge 402, not via the specimen concentration disk 101, while in the case where it is the predetermined concentration or lower, the specimen may be added to the specimen concentration disk 101 for performing the first concentration and purification, and then added from the specimen concentration disk 101 to the inside of the solid phase extraction cartridge 402 for performing purification again.

Explanation will be given below on a relation between the position and the action of a disposable container 102 of a specimen concentration disk 101, in measurement of 17β-estradiol, with reference to FIG. 3. The specimen concentration disk 101 rotates and performs installation of the disposable container 102, as well as suction/discharge and stirring of a specimen and a reagent at four positions. The position A is a position for performing the installment and the disposal of the disposable container 102 from the disposable container housing unit 103 to the specimen concentration disk 101 by the disposable container transport mechanism 104. The position B is a position for performing the discharging of the specimen transported from the specimen container 302 on the specimen disk 301 using the specimen probe 601. The position C is a position for performing the discharging of the internal standard substance, the antibody magnetic beads, the washing solution and the eluate transported from the reagent disk 201 using the reagent probe 602. In addition, at the position C, a reaction solution is sucked and disposed. Further, it is a position for performing the suction of the specimen after completion of purification using the specimen probe 601, and a treated specimen thus sucked is transported to the solid-phase extraction cartridge disk 401. It should be noted that as for a probe for performing the disposal of each solution, an exclusive probe may be installed separately from the reagent probe 602. In addition, as shown in FIG. 4, at the position C, a magnet 902 is fixed at the two side faces of the disposable container 102 for performing the separation of the washing solution and the eluate, by collecting only the magnetic beads to the magnet 902 from a suspension solution where the magnetic beads and the solution are mixed. The position D is a position for performing stirring.

Explanation will be given below on the flow of analysis. Pretreatment of a specimen is performed in the flow that firstly, concentration of the subject component to be measured using the antibody magnetic beads 901 is performed, and then, the subject component to be measured is purified using a solid-phase extraction cartridge. Firstly, an analyst sets the specimen container 302 added with a serum containing 17β-estradiol to the specimen disk 301. Then, the analyst inputs analysis items to an input unit. In the present Example, 17β-estradiol is selected and input. Based on the input information, in accordance with an analysis condition stored in the control unit in advance, analysis starts automatically.

Explanation will be given next on a concentration operation of the subject component to be measured using the antibody magnetic beads 901. The disposable container transport mechanism 104 rotates to transport the disposable container 102 from the disposable container housing unit 103 and install it at the position A of the specimen concentration disk 101.

The specimen disk 301 rotates to transfer the specimen container 302 to an operating range of the specimen probe 601. Then, the specimen is sucked and discharged at the position B of the specimen concentration disk 101.

Next, the reagent disk 201 rotates, and the reagent container 202 filled with 17β-estradiol-16,16,17-d3, which is the internal standard substance, rotates up to an operating range of the reagent probe 602, and sucks the internal standard substance. The internal standard substance is discharged in the disposable container 102 transferred at the position C in advance. Then, the specimen concentration disk 101 rotates, the disposable container 102 rotates up to the position D, and stirring is performed.

Subsequently, the reagent disk 201 rotates, and the reagent container 202 filled with a suspension solution of the antibody magnetic beads 901, transfers to the operating range of the reagent probe 602, and sucks the suspension solution of the antibody magnetic beads 901. The suspension solution of the antibody magnetic beads 901 is discharged in the disposable container 102 which has been transferred to the position C in advance. Then, the specimen concentration disk 101 rotates up to the position D and stirring is performed. Here, the 17β-estradiol and 17β-estradiol-16,16,17-d3 are captured specifically to the antibody magnetic beads 901.

Figure 5:
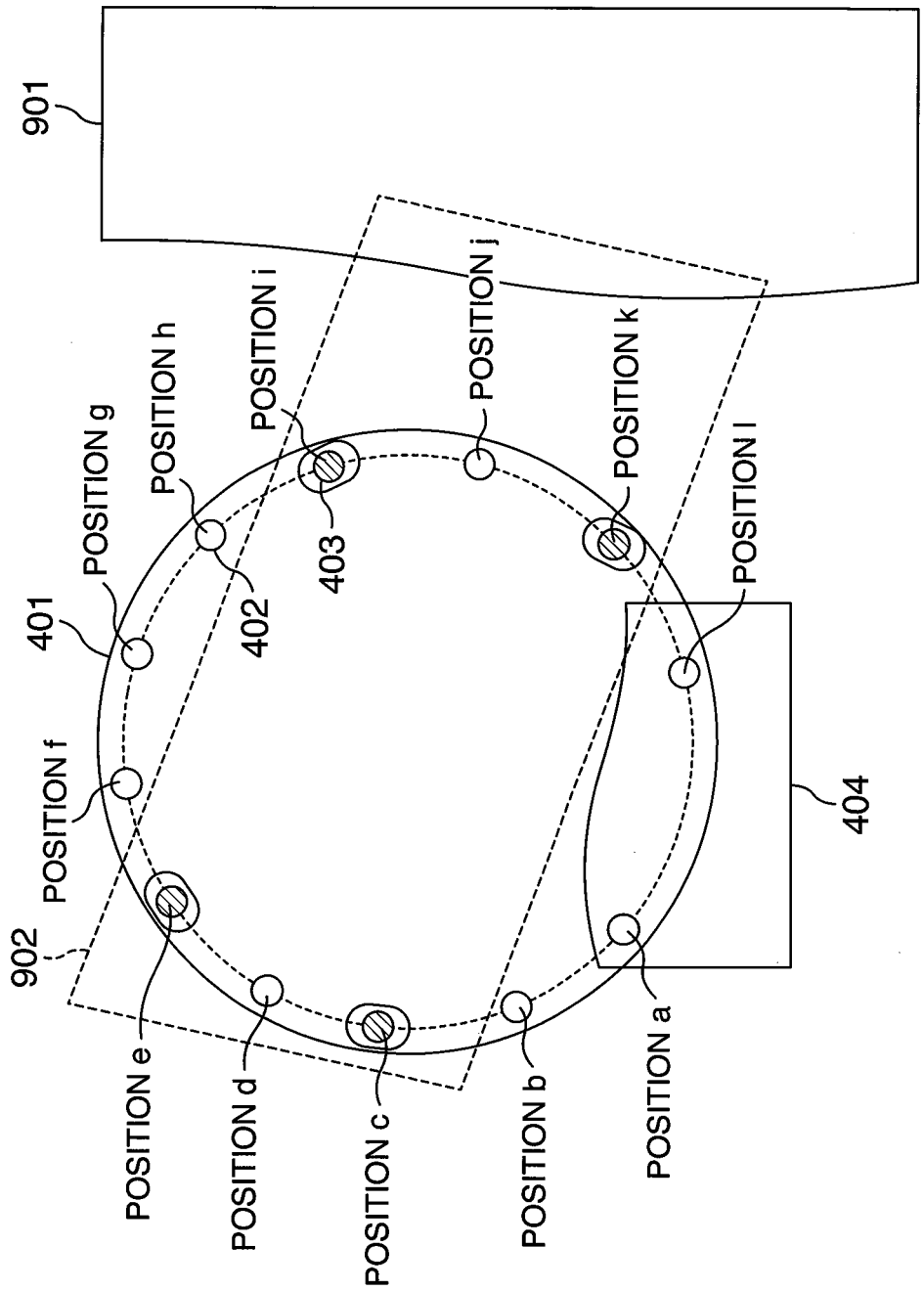
FIG. 5 is a drawing illustrating relation between position and action of a solid-phase extraction cartridge of a solid-phase extraction cartridge disk.

Subsequently, the specimen concentration disk 101 rotates, and the disposable container 102 rotates up to the position C. As shown in FIG. 5, the antibody magnetic beads 901 are collected at the wall surface of the disposable container 102 by magnetic force of the magnet 902 fixed at the side surface of the disposable container 102. A solution in the disposable container 102 is sucked using the reagent probe 602 and disposed.

Subsequently, the reagent disk 201 rotates, and the reagent container 202 filled with 100 mmol/L of ammonium acetate, which is a first washing solution, transfers up to the operating range of the reagent probe 602, and sucks 100 μL of ammonium acetate. Then, the ammonium acetate is discharged in the disposable container 102 which has been transferred to the position C in advance. Then, the specimen concentration disk 101 rotates up to the position D, and stirring is performed. Then, the specimen concentration disk 101 rotates, and the disposable container 102 rotates up to the position C, and similarly as above, the antibody magnetic beads 901 are collected using the magnet 902, and a solution in the disposable container 102 is sucked using the reagent probe 602 and disposed.

Subsequently, the reagent disk 201 rotates, and the reagent container 202 filled with $H_2O$, which is a second washing solution, transfers up to the operating range of the reagent probe 602, and sucks 100 μL of $H_2O$. Then, $H_2O$ is discharged into the disposable container 102 which has been transferred to the position C in advance. Then, the specimen concentration disk 101 rotates to the position D, and stirring is performed. Then, the specimen concentration disk 101 rotates, and the disposable container 102 rotates up to the position C, and similarly as above, the antibody magnetic beads 901 are collected using the magnet 902, and a solution in the disposable container 102 is sucked using the reagent probe 602 and disposed.

Subsequently, the reagent disk 201 rotates and the reagent container 202 filled with 2% of acetic acid, which is an eluate, and transfers up to the operating range of the reagent probe 602, and sucks the aqueous solution of acetic acid. Then, the aqueous solution of acetic acid is discharged in the disposable container 102 which has been transferred to the position C in advance. Then, the specimen concentration disk 101 rotates up to the position D, and stirring is performed. Here, the 17β-estradiol and 17β-estradiol-16,16,17-d3, which have been captured by the antibody magnetic beads 901, are isolated and eluted in the aqueous solution of acetic acid. Then, the specimen concentration disk 101 rotates, and the disposable container 102 rotates up to the position C, and the antibody magnetic beads 901 are collected using the magnet 902, and a solution in the disposable container 102 is sucked using the reagent probe 602. Then, the reagent probe 602 rotates up to the solid-phase extraction cartridge 402 on the solid-phase extraction cartridge disk 401, and the solution is discharged to the solid-phase extraction cartridge 402, at the sample addition position on the solid-phase extraction cartridge disk 401. It should be noted that ammonium acetate and water were used as the washing solution, however, washing may be omitted or may be performed a plurality of times, depending on the purification degree required. Acetic acid was used as the eluate, however, the subject component to be measured may be isolated from the magnetic beads by alkaline treatment or ionic strength treatment, other than acidic treatment using formic acid or hydrochloric acid or the like.

By a series of flow as above, on the specimen concentration disk 101, the purification of the 17β-estradiol and 17β-estradiol-16,16,17-d3 is performed from a serum sample. In the present analysis device, in addition to hormones such as testosterone, aldosterone, thyroxine, triiodothyronine, for example, anticancer drugs such as trastuzumab, irinotecan, anti-HIV drugs such as saquinavir, ritonavir, and a metabolite thereof can be purified.

Explanation will be given next on purification of the subject component to be measured using the solid-phase extraction cartridge, with reference to FIG. 5. FIG. 5 is a drawing illustrating a relation between the position and the action of a solid-phase extraction cartridge of a solid phase extraction cartridge disk.

The solid-phase extraction is composed of 5 steps, and specifically each step is (1) a step for conditioning the solid phase for passing through an organic solvent to the solid phase, (2) a step for equilibrating the solid phase making an aqueous solvent pass through to the solid phase, (3) a step for holding the subject component to be measured to the solid phase by passing through a sample to the solid phase, (4) a step for washing for passing through water to the solid phase, and (5) a step for making the subject component to be measured elute from the solid phase by passing through the organic solvent to the solid phase.

Firstly, explanation will be given on the conditioning step of the solid phase for passing through an organic solvent to the solid phase. The solid-phase extraction cartridge 402 is transported and installed from the consumable housing unit 404 to the position "a" of the solid phase extraction cartridge disk 401. Then the solid-phase extraction cartridge 402 on the solid-phase extraction cartridge disk 401 rotates to the position "b", and 200 µL of methanol is added from a methanol dispenser (not depicted) to the solid-phase extraction cartridge 402. Then the solid-phase extraction cartridge 402 on the solid-phase extraction cartridge disk 401 rotates to the position "c" and the pressure loading unit 403 is closely adhered to the upper part of the solid-phase extraction cartridge 402 and pressurized, and the conditioning of the solid phase is completed by passing through the methanol to the solid-phase extraction cartridge 402. The methanol which is an eluted waste drops into a saucer 1002, which is positioned beneath the solid-phase extraction cartridge 402 and can receive the eluates from the positions "c", "e", "i" and "k". This saucer 1002 is inclined from a horizontal direction so as to provide a mechanism in which the eluate freely flows into a waste liquid tank 1001.

Explanation will be given next on the equilibration step of the solid phase making an aqueous solvent pass through to the solid phase. The solid-phase extraction cartridge 402 on the solid-phase extraction cartridge disk 401 rotates to the position "d", and 200 µL of water is added from a water dispenser (not depicted) to the solid-phase extraction cartridge 402. Next, the solid-phase extraction cartridge 402 on the solid-phase extraction cartridge disk 401 rotates to the position "e", and the pressure loading unit 403 is closely adhered to the upper part of the solid-phase extraction cartridge 402 and pressurized, and the equilibration step of the solid phase is completed by passing through the water to the solid phase extraction cartridge 402.

Subsequently, explanation will be given on the holding step to the solid phase of the subject component to be measured making a sample pass through to the solid phase. In synchronization with the timing that the solid-phase extraction cartridge 402 on the solid-phase extraction cartridge disk 401 rotates to the position "f", the specimen for which the purification of the subject component to be measured has been completed at the specimen concentration disk 101, is sucked using the reagent probe 602, and discharged to the solid-phase extraction cartridge 402 at the position "f". Then, the solid-phase extraction cartridge 402 on the solid-phase extraction cartridge disk 401 rotates to the position "g", and the pressure loading unit 403 is closely adhered to the upper part of the solid-phase extraction cartridge 402 and pressurized, and the holding step of the subject component to be measured to the solid phase is completed by passing through a solution containing a sample to the solid-phase extraction cartridge 402.

Subsequently, explanation will be given on the washing step making water pass through to the solid phase. In synchronization with the timing that the solid phase extraction cartridge 402 on the solid phase extraction cartridge disk 401 rotates to the position "h", 200 µL of water is added from a water dispenser to the solid-phase extraction cartridge 402.

Next, the solid-phase extraction cartridge 402 on the solid phase extraction cartridge disk 401 rotates to the position "i", and the pressure loading unit 403 is closely adhered to the upper part of the solid-phase extraction cartridge 402 and pressurized, and the step for washing is completed by passing through water to the solid-phase extraction cartridge 402.

Subsequently, explanation will be given on the step for making the subject component to be measured elute from the solid phase by passing through the organic solvent to the solid phase. In synchronization with the timing that the solid-phase extraction cartridge 402 on the solid-phase extraction cartridge disc 401 rotates to the position "j", 100 µL of methanol is added from a methanol dispenser to the solid-phase extraction cartridge 402. Then, in synchronization with the timing that the solid-phase extraction cartridge 402 on the solid-phase extraction cartridge disk 401 rotates to the position "k", the saucer container 502 is transported from the consumable housing unit 404 to the position "k" of the saucer disk 501, and installed. After that, the pressure loading unit 403 is closely adhered to the upper part of the solid-phase extraction cartridge 402 and pressurized, and the sample pass through the solid-phase extraction cartridge 402, and the sample after solid-phase extraction is eluted to the saucer container 502. Then, the solid-phase extraction cartridge 402 on the solid-phase extraction cartridge disc 401 rotates to the position "l", and disposal of the cartridge is performed.

The saucer container 502 holding a specimen after the completion of pretreatment rotates up to a drive position of the pretreated specimen introduction mechanism 701, and the specimen after the completion of pretreatment sucked from the saucer container 502 is introduced to the mass spectrometry unit 801. Parameters of Q1/Q3 of a mass spectrometer are set as follows: Q1/Q3=271/145 for 17β-estradiol which was ionized by a negative mode, and Q1/Q3=274/148 for 17β-estradiol-16,16,17-d3, and an ion amount detected is output as a measurement value. By fitting this output value to a calibration curve data of a QC (quality control) sample stored in the control unit in advance, a quantitative value of 17β-estradiol which is the subject component to be measured is calculated.

In this way, the analysis device of the present invention has a mechanism for performing concentration of the subject component to be measured by the principle of antigen-antibody reaction, using the antibody magnetic beads on the specimen concentration disk 101, at the former stage of solid-phase extraction processing. In this way, it becomes possible to detect even in the subject component to be measured in a low concentration region, for example, hormones having a blood concentration of about ng/mL, whose quantification has been difficult by conventional analysis devices for detecting using a mass spectrometer after a solid-phase extraction treatment as pretreatment. In addition, for the arrangement of 5 disks and the probes for transporting the specimen and the reagent between each of the disks, by not making them exclusive by each disk, and by common use of functions, higher precision and lower cost analysis can be realized without making the device larger.

REFERENCE SIGNS LIST 101 specimen concentration disk
102 disposable container
103 disposable container housing unit
104 disposable container transport mechanism
201 reagent disk
202 reagent container
301 specimen disk
302 specimen container
401 solid-phase extraction cartridge disk
402 solid-phase extraction cartridge
402a cartridge main body
402b upper stage filter
402c lower stage filter 402d solid-phase extraction agent
403,403c pressure loading unit
403a pressure loading unit holder
403b syringe for pressurization
404 consumable housing unit
501 saucer disk
502 saucer container
601 specimen probe
602 reagent probe
701 pretreated specimen introduction mechanism
801 mass spectrometry unit
901 antibody magnetic beads
902 magnet
1001 waste liquid tank
1002 saucer

The invention claimed is:

1. An analysis device, comprising:
a specimen disk equipped with specimen containers;
a reagent disk equipped with reagent containers;
a plurality of first containers;
a plurality of second containers;
a first disk configured to hold the plurality of first containers used to perform a first purification using an antigen-antibody reaction of a subject component to be measured of a specimen;
a second disk equipped with the plurality of second containers used to perform a second purification using a solid-phase extraction of the specimen purified in the first containers of the first disk;
a mass spectrometry unit which measures the specimen purified in the plurality of second containers on the second disk;
a magnet disposed at a third position of the first disk;
a stirring mechanism disposed at a fourth position of the first disk, beyond a range of a magnetic force of the magnet;
one or more probes used for dispensing and suctioning; and
a controller programmed to control at least the first disk, the second disk, the stirring mechanism, and the dispensing and suctioning by the one or more probes to:
provide one of the plurality of first containers onto the first disk at a first position of the first disk,
discharge a specimen into the one first container on the first disk at a second position of the first disk,
discharge an internal standard substance into the one first container at the third position of the first disk,
stir contents of the one first container, using the stirring mechanism, at the fourth position of the first disk,
discharge magnetic beads into the one first container at the third position of the first disk,
discharge a first washing solution into the one first container at the third position of the first disk,
discharge a second washing solution into the one first container at the third position of the first disk,
discharge an elute solution into the one first container at the third position of the first disk,
retain the antibody magnetic beads against a wall surface of the one first container at the third position of the first disk, and suction and dispose a solution within the one first container at the third position by a probe of the one or more probes, and
suction a solution in the one first container and dispense the solution into one of the plurality of second containers of the second disk using the one or more probes,
wherein the controller is further programmed to perform the second purification of the solution in the one second container using solid-phase extraction.

2. The analysis device according to claim 1, wherein the one or more probes comprise:
a first probe accessible to the specimen containers, the plurality of first containers and the plurality of second containers; and
a second probe accessible to the reagent containers, the plurality of first containers and the plurality of second containers,
wherein each of the first and second probes performs suction and discharge of a solution in each of the containers.

3. The analysis device according to claim 1, wherein,
a third disk equipped with third containers which house the specimen purified in the plurality of second containers of the second disk is arranged lower than the second disk, and a purified specimen dripped from the one second container is housed in one of the third containers.

4. The analysis device according to claim 1, wherein,
in the case where analysis of a specimen having a specimen concentration of a first predetermined value or lower is performed, purification of the specimen in the specimen containers is performed in the one first container, and purification of the specimen purified in the one first container is performed in the one second container; and
in the case where analysis of the specimen having a specimen concentration of a second predetermined value or higher is performed, purification of the specimen in one of the specimen containers is performed in the one second container.

5. The analysis device according to claim 1, wherein:
in the case where analysis of the specimen having a specimen concentration of a first predetermined value or lower is performed, a first reagent in one of the reagent containers is discharged to an inside of the one first container where the specimen is housed, and a second reagent in the one of the reagent containers is discharged to an inside of the one second container where the purified specimen is housed, and
in the case where analysis of the specimen having a specimen concentration of a second predetermined value or higher is performed, the second reagent in one of the reagent containers is discharged to the inside of the one second container where the specimen is housed.

6. The analysis device according to claim 1, wherein the first disk comprises a temperature adjustment mechanism which maintains a set temperature of the contents of the plurality of first containers of the first disk.

7. The analysis device according to claim 1, wherein
the controller is programmed to control at least the first disk, the second disk, the stirring mechanism, and the dispensing and suctioning by the or more probes to:
(a) provide another first container onto the first disk at a first position of the first disk,
after (a), (b) discharge a specimen into the another first container on the first disk at a second position of the first disk,
after (b), (c) discharge an internal standard substance into the another first container at the third position of the first disk,
after (c), (d) stir contents of the another first container, using the stirring mechanism, at the fourth position of the first disk,
after (d), (e) discharge magnetic beads into the another first container at the third position of the first disk,
after (e), (f) stir contents of the another first container, using the stirring mechanism, at the fourth position of the first disk, after (f), (g) discharge a first washing solution into the another first container at the third position of the first disk, after (g), (h) stir contents of the another first container, using the stirring mechanism, at the fourth position of the first disk, after (h), (i) discharge a second washing solution into the another first container at the third position of the first disk, after (i), (j) stir contents of the another first container, using the stirring mechanism, at the fourth position of the first disk, after (j), (k) discharge an elute solution into the another first container at the third position of the first disk, and after (k), (l) stir contents of the another first container, using the stirring mechanism, at the fourth position of the first disk.

* * * * *